US00PP14390P39

(12) United States Plant Patent
Olesen et al.

(10) Patent No.: US PP14,390 P3
(45) Date of Patent: Dec. 23, 2003

(54) MINIATURE ROSE PLANT NAMED 'POULFLAG'

(50) Latin Name: *Rosa hybrida*
Varietal Denomination: POULflag

(75) Inventors: L. Pernille Olesen, Fredensborg (DK); Mogens N. Olesen, Fredensborg (DK)

(73) Assignee: Poulsen Roser APS, Fredensborg (DK)

( * ) Notice: Subject to any disclaimer, the term of this patent is extended or adjusted under 35 U.S.C. 154(b) by 170 days.

(21) Appl. No.: 09/776,156

(22) Filed: Feb. 2, 2001

(65) Prior Publication Data

US 2002/0152511 P1 Oct. 17, 2002

(51) Int. Cl.[7] ..... A01H 5/00

(52) U.S. Cl. ..... Plt./119

(58) Field of Search ..... Plt./119, 116, 120, Plt./126

(56) References Cited

U.S. PATENT DOCUMENTS

PP12,484 P2 * 3/2002 Olesen et al. ..... Plt./119

* cited by examiner

*Primary Examiner*—Bruce R. Campell
*Assistant Examiner*—June Hwu

(57) ABSTRACT

A new miniature rose plant which has abundant, bright orange flowers and attractive foliage. This new and distinct variety has shown to be uniform and stable in the resulting generations from asexual propagation.

1 Drawing Sheet

SUMMARY OF THE INVENTION

Classification

Botanical.—*Rosa hybrida* 'POULflag'.

Commercial.—Miniature.

The present invention constitutes a new and distinct variety of miniature rose plant which originated from a controlled crossing between 'POULneto' and 'Rumba', both unpatented varieties. The two parents were crossed during the summer of 1996 and the resulting seeds were planted in a controlled environment in Fredensborg, Denmark. The new variety is named 'POULflag'.

The new rose may be distinguished from its seed parent, 'POULneto', by the following combination of characteristics:

1. 'POULflag' has bright orange blooms, whereas the seed parent has soft peach blooms.
2. 'POULflag' is a miniature garden rose, whereas 'POULneto' is utilized in cut-flower production.
3. 'POULflag' exhibits more compact and vigorous growth than the seed parent.

The new variety may be distinguished from its pollen parent, 'Rumba' by the following combination of characteristics:

1. 'POULflag' has bright orange flowers, whereas 'Rumba' has bi-color (yellow/red) flowers.
2. 'POULflag' is suitable for pot rose production, while 'Rumba' is utilized in cut-flower production.
3. 'POULflag' is more compact, even and vigorous in growth when compared 'Rumba'.

The objective of the hybridization of this rose variety was to create a new and distinct variety for garden use with unique qualities, such as:

1. Uniform and abundant flowers;
2. Vigorous and compact growth when propagated by cuttings;
3. Disease resistance.

This combination of qualities is not present in previously available commercial cultivars of this type and distinguish 'POULflag' from all other varieties of which we are aware.

As part of their rose development program, L. Pernille Olesen and Mogens N. Olesen germinated the seeds from the aforementioned hybridization during winter 1996 and conducted evaluations on the resulting seedlings in a controlled environment in Fredensborg, Denmark.

'POULflag' was selected in the spring of 1997 by the inventors as a single plant from the progeny of the aforementioned hybridization. Asexual reproduction of 'POULflag' by traditional budding and rooted cuttings was first done by L. Pernille and Mogens N. Olesen in their nursery in Fredensborg, Denmark in summer 1997. This initial and other subsequent asexual propagations conducted in controlled environments have demonstrated that the characteristics of 'POULflag' are true to type and are transmitted from one generation to the next.

BRIEF DESCRIPTION OF THE DRAWING

The accompanying color illustration shows as true as is reasonably possible to obtain in color photographs of this type the variety rose 'POULflag'. Specifically illustrated in SHEET 1 include:

1. Rose plant exhibiting foliage, leaves, and leaflets.
2. Flower bud, partially opened bud, and open bloom;
3. General plant growth and habit.

DETAILED DESCRIPTION OF THE VARIETY

The following is a description of 'POULflag', as observed in its growth in Jackson County, Oreg., on plants aged eighteen weeks. Color references are made using The Royal Horticultural Society (London, England) Colour Chart, 1995, except where common terms of color are used.

For a comparison, several physical characteristics of the rose variety 'POULfiry', a rose variety from the same inventors described and illustrated in U.S. Plant Pat. No. 12,484 and issued Mar. 26, 2002 are compared to 'POULflag' in Chart 1.

CHART 1

| | 'POULflag' | 'POULfiry' |
|---|---|---|
| Color of petal, inner side, middle zone, upon opening. | Orange Group 28A to Yellow Group 13A | Red Group 40B. |
| Petalage | 15–25 | 20–25 |
| Upon opening, color basal petal spot, outer side. | Yellow-Orange Group 13B | Yellow-Orange Group 22B. |

Parents:

*Seed parent.*—'POULneto'.

*Pollen parent.*—'Rumba'.

FLOWER AND FLOWER BUD

Blooming habit: Continuous.

Flower bud:

*Bud form.*—Long, pointed ovate.

*Size.*—Upon opening, 27 to 33 mm in length from base of receptacle to end of bud.

*Bud color.*—As sepals unfold, Orange-Red Group 33A and Orange Group 28A. At ¼ open, Orange-Red Group 33A and Orange Group 28A.

*Sepals.*—Length: 16 to 18 mm. Width: 8 to 10 mm. Color: Upper surface is Yellow-Green Group 144B and 144C. Lower surface is Yellow-Green Group 144B. Appendages: Weak foliaceous appendages on 4 of the five sepals. Pubescence: Moderate. Stipitate Glands: Many stipitate glands present on sepal margins and undersides.

*Receptacle.*—Surface: Smooth. Shape: Funnel-shaped. Size: 6 mm (h)×8 mm (w). Color: Green Group 144A with anthocyanin intonations of Greyed-Red Group 180C.

*Peduncle.*—Surface: Some stipitate glands present. Length: 30 to 40 mm long. Color: Yellow-Green Group 144B. Strength: Strong. Anthocyanin: Greyed-Orange Group 180C.

*Borne.*—Multiple (7–10) buds per stem.

Flower bloom:

*Fragrance.*—Light floral scent.

*Duration.*—As a pot plant, flowers last from 12 to 15 days.

*Size.*—Medium. Average flower diameter is 50 mm when open.

*Form.*—Shape of flower when viewed from the side: Upon opening, upper part: Convex. Upon opening, lower part: Flattened convex. After opening, upper part: Flattened convex. After opening, lower part: Concave. Petalage: Semi-double. Average range: 15 to 25 petals, with 3 to 5 petaloids.

Color:

*Upon opening, petals.*—Inner Side: Middle zone: Orange Group 28A to Yellow Group 13A. Marginal zone: Orange Group 28A to Red Group 40B. Basal petal spot: Yellow-Orange Group 14B. Outer side: Middle zone: Orange Group 24B. Marginal zone: Orange Group 24B to Red Group 40C Basal petal spot: Yellow Group 13B.

*Upon opening, basal petal spots.*—Upper surface: Yellow Group 13B. Lower surface: Yellow Group 6C.

*After opening, petals.*—Outermost petals: Inner Side: Middle zone: Orange Group 28A to Yellow Group 13A. Marginal zone: Orange Group 28A to Red Group 40B. Basal petal spot: Yellow-Orange Group 14B. Outer side: Middle zone: Orange Group 24B. Marginal zone: Orange Group 24B to Red Group 40C Basal petal spot: Yellow Group 13B.

*After opening, basal petal spots.*—Upper surface: Yellow Group 11A. Lower surface: Yellow Group 3A.

General tonality: On open flower, Orange Group 28A. No change in the general tonality at the end of the $7^{th}$ day. Orange Group 28A.

Petals:

*Petal size.*—Petals are 25 to 30 mm long and 25 mm wide.

*Petal reflex.*—Moderate.

*Petal edge.*—Entire, with point in center of margin.

*Shape.*—Obovate.

*Petaloids.*—3 to 5. Petaloids are 12 mm long and 7 mm wide. Petaloid coloration is Orange Group 28A on both upper and lower surfaces.

*Thickness.*—Thin.

*Arrangement.*—Not imbricated.

Reproductive organs:

*Filaments.*—Color: Yellow-Orange Group 17A. Length: 5 to 9 mm.

*Pistils.*—Length: 5 to 9 mm. Quantity: 40.

*Pollen.*—Color: Yellow-Orange Group 17A. Quantity: Scant.

*Anthers.*—Length: 2 to 3 mm. Color: Yellow-Orange Group 18B. Quantity: 35 to 40.

*Stigmas.*—Height:Stigmas are even in height relative to anthers. Color: Yellow Group 7C.

*Styles.*—Color: Yellow-Green Group 150D.

*Hips.*—None observed.

PLANT

Plant growth: Vigorous and compact in growth. When grown in a 12–15 cm pot, the average height of the plant is 25–30 cm and the average width is 40–60 cm.

Stems:

*Color.*—Young wood: Yellow-Green Group 144B. Older wood: Yellow-Green Group 144B.

*Thorns.*—Incidence: 6 thorns per 10 cm of stem. Size: Average length is 7 mm. Color: Greyed-Yellow Group 160C on Bottom; Greyed-Red group 179A on top. Shape: Concave.

Plant foliage:

*Number of leaflets on normal leaves in middle of a stem.*—5.

*Leaf size.*—125 mm (l) by 90 mm (w).

*Quantity.*—Average.

*Color.*—Mature foliage: Upper Leaflet Surface:Green Group 137A. Lower Leaflet Surface:Green Group 138B. Juvenile foliage: Upper Leaflet Surface:Green Group 137A. Lower Leaflet Surface:Green Group 138B. Anthocyanin intonation: None noted.

Plant leaflets:

*Stipule.*—Length: 14 mm. Color: Yellow-Green Group 144B. Anthocyanin: Greyed-Red Group 178A. Margins: Some stipitate glands present.

*Petiole.*—Length: 15 mm. Color: Green Group 144A. Underneath: Green Group 144A. Stipitate glands and occasionally a single, small thorn. Margins: Stipitate glands present. Anthocyanin: None observed.

*Rachis.*—Length: 15 mm. Color: Green Group 144A. Underneath: Green Group 144A. Stipitate glands and occasionally a single, small thorn. Margins: Stipitate glands present. Anthocyanin: None observed.

*Leaflet.*—Edge: Serrated. Shape: Ovate. Surface: Moderately glossy. Texture: Thin. Arrangement: Odd pinnate. Venation: Reticulate.

Disease resistance: Above average resistance to mildew, rust, black spot, and Botrytis under normal growing conditions in Jackson County, Oreg.

Cold hardiness: The variety 'POULflag' has been found to be resistant to damage from cold in USDA Zone 7.

We claim:

1. A new and distinct variety of rose plant of the miniature rose class, substantially as herein illustrated and described as a distinct and novel rose variety due to its abundant bright orange flowers, disease resistance, and extended period of bloom.

* * * * *

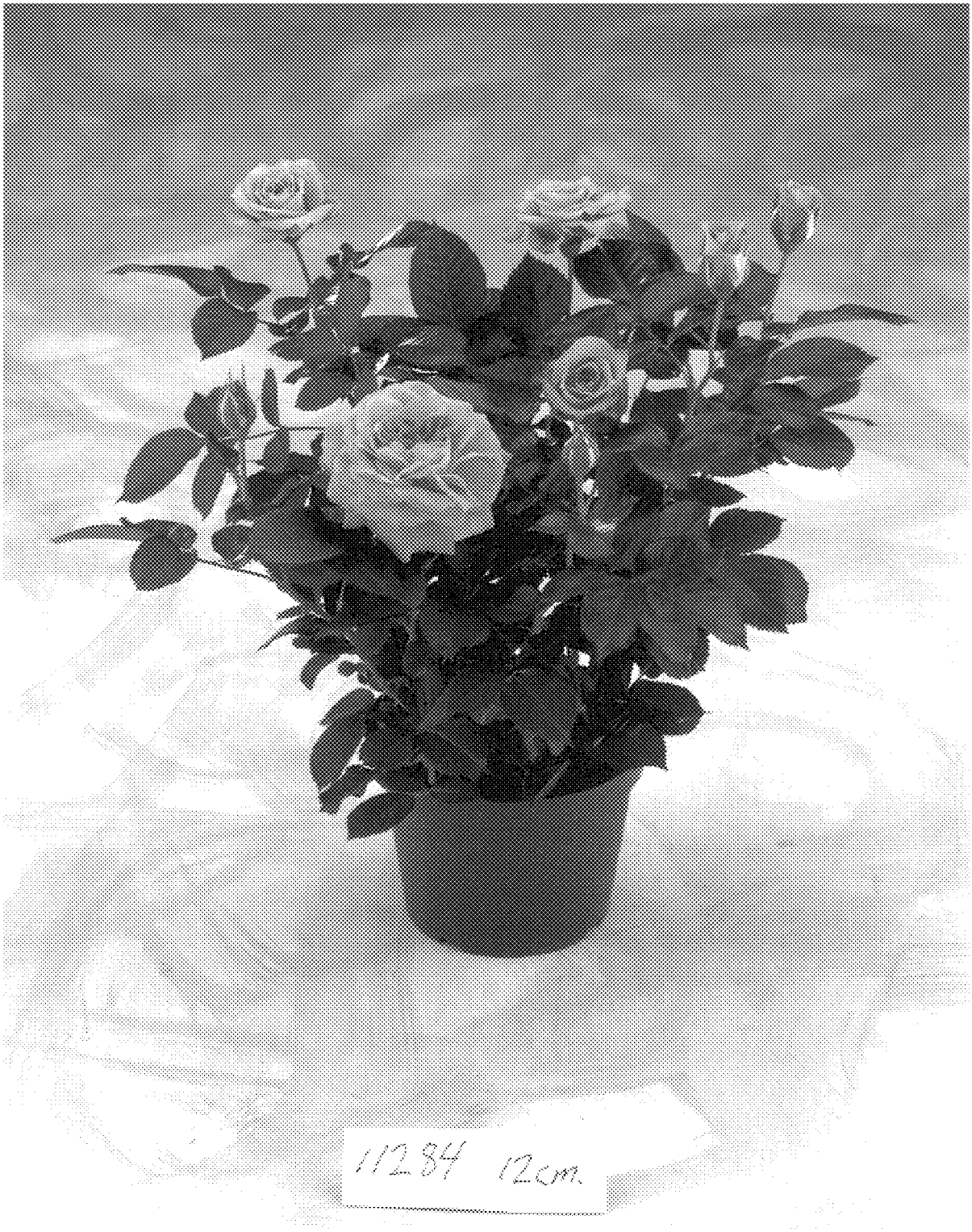
11284 12cm.